(12) United States Patent
Metzger

(10) Patent No.: US 6,620,140 B1
(45) Date of Patent: Sep. 16, 2003

(54) METHOD AND AN APPARATUS FOR A PORT ACCESS SYSTEM

(75) Inventor: Anja Metzger, Stillwater, MN (US)

(73) Assignee: Ethicon, Inc., Somerville, NJ (US)

( * ) Notice: Subject to any disclaimer, the term of this patent is extended or adjusted under 35 U.S.C. 154(b) by 139 days.

(21) Appl. No.: 09/607,873

(22) Filed: Jun. 30, 2000

(51) Int. Cl.⁷ ................................................ A61K 9/02
(52) U.S. Cl. ........................ 604/288.01; 604/288.02; 604/288.04; 604/93.01; 604/502
(58) Field of Search .................. 604/288.01, 288.02, 604/288.03, 288.04, 891.1, 502, 93.01, 175, 272, 506

(56) References Cited

U.S. PATENT DOCUMENTS

| | | | | |
|---|---|---|---|---|
| 4,886,499 A | * | 12/1989 | Cirelli et al. | 604/131 |
| 5,185,003 A | * | 2/1993 | Brethauer | 604/93 |
| 5,556,381 A | * | 9/1996 | Ensminger et al. | 604/93 |
| 5,637,088 A | * | 6/1997 | Wenner et al. | 604/93 |
| 5,848,990 A | * | 12/1998 | Cirelli et al. | 604/136 |
| 5,931,801 A | * | 8/1999 | Burbank et al. | 604/4 |
| 6,007,516 A | * | 12/1999 | Burbank et al. | 604/93 |
| 6,090,068 A | * | 7/2000 | Chanut | 604/93 |
| 6,238,375 B1 | * | 5/2001 | Powell | 604/263 |

\* cited by examiner

Primary Examiner—Thomas Denion
Assistant Examiner—Binh Tran
(74) Attorney, Agent, or Firm—Blakely, Sokoloff, Taylor & Zafman LLP

(57) ABSTRACT

An apparatus comprising a housing having a port adapted to receive a moveable first member and a moveable second member is configured to communicate with a tube.

9 Claims, 11 Drawing Sheets

METHOD AND AN APPARATUS FOR A PORT ACCESS SYSTEM

BACKGROUND OF THE INVENTION

1. Field of the Invention

This invention relates generally to intravascular assemblies, and more specifically to a port or implantable pump access system.

2. Background

Intravascular devices such as port access systems are generally used for passing fluids between a device such as a syringe or a drip to or from body lumens such as veins or arteries, or other internal target sites. Such an assembly usually includes a means for transferring fluids to a needle such as a tube. The sharp tip of the needle is used for piercing a body lumen so that access may be gained into the body lumen by the needle. Once the needle is located within the body lumen, the needle is removed and discarded while the tube remains in the body lumen.

Current port access systems involve insertion of a non-coring needle or huber needle that is winged or the standard type of needle into a port secured to a patient. Once the needle is inserted into the patient, the wings of the port access system are taped down and used for infusion of liquids. The needle is removed manually which sometimes results in the needle inadvertently repuncturing the patient's skin or causes an accidental needle stick to the healthcare worker. It is desirable to have a port access system that allows infusion of liquids into a patient but also reduces the risk of an inadvertent needle puncture to a healthcare worker or to the patient.

SUMMARY

An apparatus and a method are disclosed comprising a housing having a port adapted to receive a moveable first member. A moveable second member is configured to communicate with a tube. Additional features, embodiments, and benefits will be evident in view of the figures and detailed description presented herein.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

A port access system is disclosed that includes a housing having a port that is adapted to receive a moveable first member coupled to a moveable second member. The moveable second member is configured to communicate with a tube.

The port access system described herein offers several improvements over conventional port access systems. Conventional port access systems involve insertion of a non-coring needle or huber needle that is inserted into a patient and the wings are taped down for infusion of fluids. Because removal of a needle involves a manual process, a patient or a health care worker may be inadvertently harmed by the needle. One aspect of the invention is that the needle is coupled to a moveable member that inserts the needle into the body of the patient and also is able to remove the needle from the patient. This process occurs within the housing of the port access system. This device generally prevents the healthcare worker or the patient from being punctured by a used needle. The following detailed description and accompanying drawings are provided for the purpose of describing and illustrating presently preferred embodiments of the invention only and are not intended to limit the scope of the invention.

Figure 1:
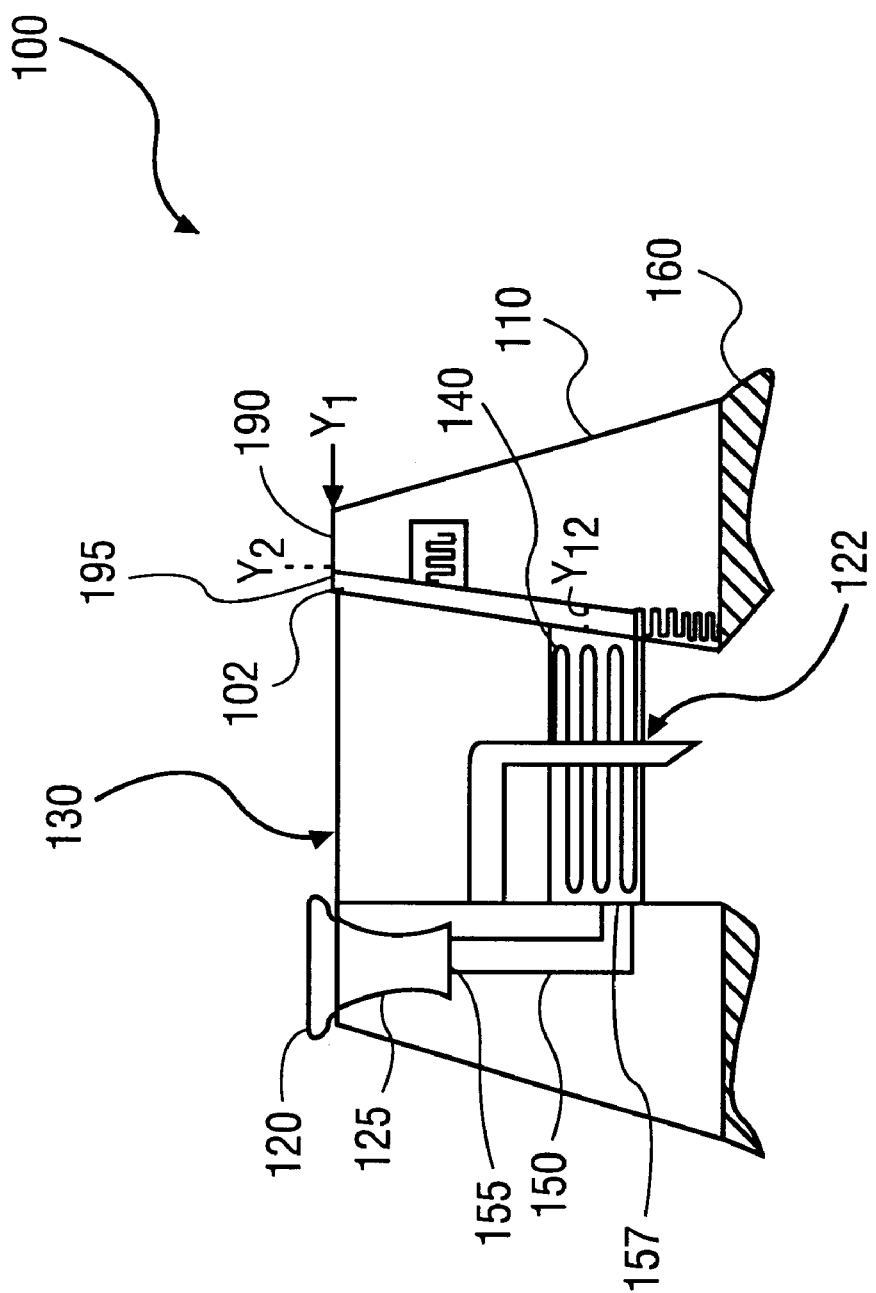
FIG. 1 illustrates a port access system in which a moveable member is in a first position in accordance with one embodiment of the invention.

FIGS. 1 through 6 illustrate port access system 100 in its deactivated state and its activated state. FIG. 1 illustrates a port access system 100 in a deactivated state in accordance with one embodiment of the invention. Port access system 100 includes housing 110 in which moveable first member 122, moveable second member 130, and third moveable member 102 are located and are connected to housing 110 using conventional means such as securing the moveable members to housing 110 using a strong adhesive, screws, or other suitable means. Alternatively, housing 110 may be configured such that the second moveable member 130, for example, may have sides configured such that the sides of second moveable member 130 slide into a receiving side of housing 110.

FIG. 1 shows housing 110 adapted to receive a moveable first member and a moveable second member 130. Housing 110 has a diameter approximately in the range of ¼ to ¾ inches. Housing 110 provides a secure location for an access needle. Housing 110 is placed on the patient's chest such that housing 110 surrounds the site in which first member 122 such as a coring or huber needle is used to pierce the patient's skin.

Housing 110 has wings 160 formed at one end of housing 110. Adhesive may be deposited or placed at the bottom surface of wings 160 which is the surface that is generally opposed to the patient's body. Adhesives such as an acrylic adhesive may be applied to the bottom of a pad made of closed cell foam attached to the underside of the device for patient comfort. Examples of such adhesives are found in Band-Aid™ or Bioclusive™. The bottom surface of wings 160 is placed onto the patient's skin thereby supporting the port access system 100 against the patient's body. Housing 110 is coupled to port 120. Inlet 155 of port 120 connected to housing 110 allows fluids to flow in through tube 150 and exit outlet of non-coring needle 157. Port 120 opens to a funnel-like body 125. Port 120 also communicates with tube 150.

Figure 2:
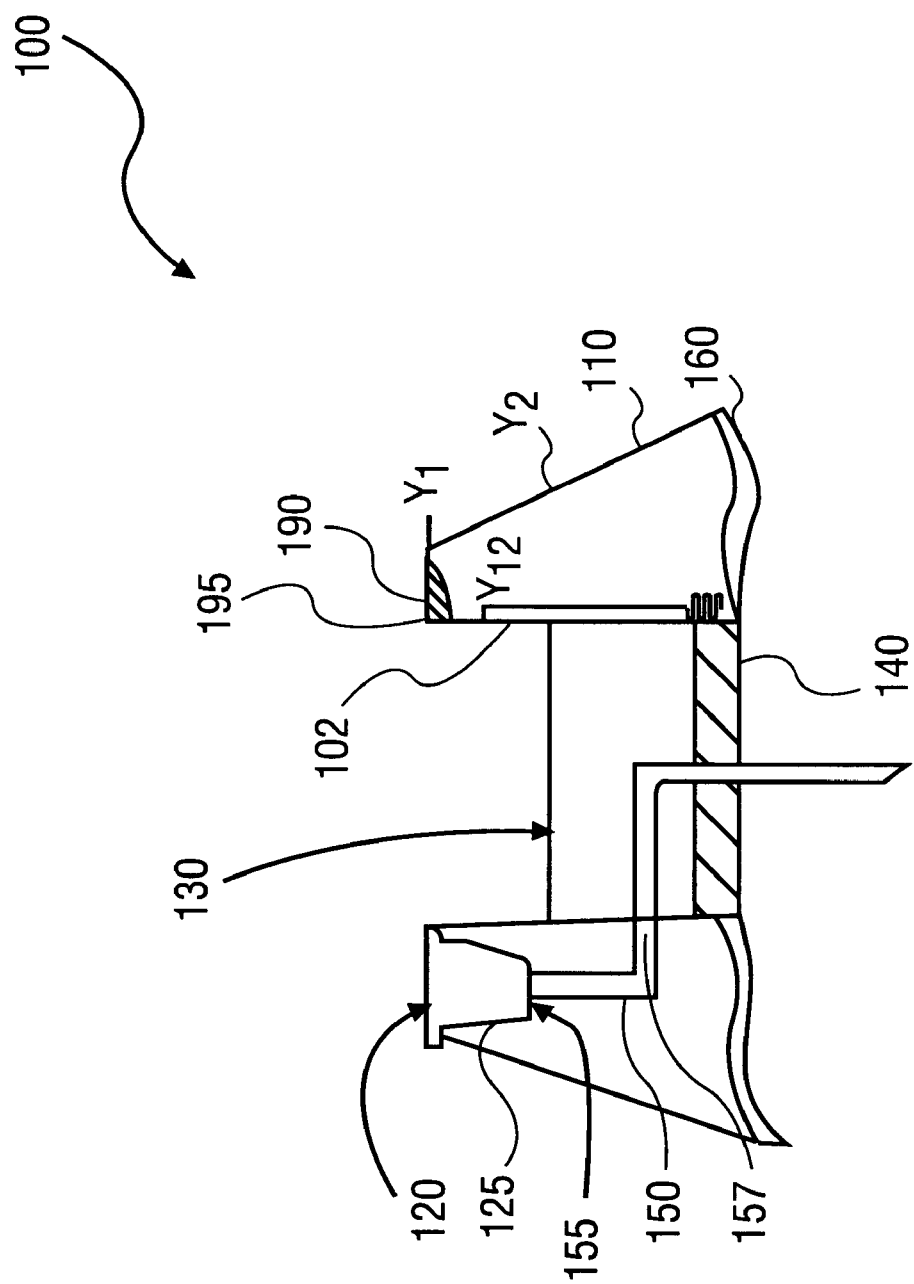
FIG. 2 illustrates a port access system in which the moveable member advances from one position to another position in accordance with one embodiment of the invention.
Figure 3:
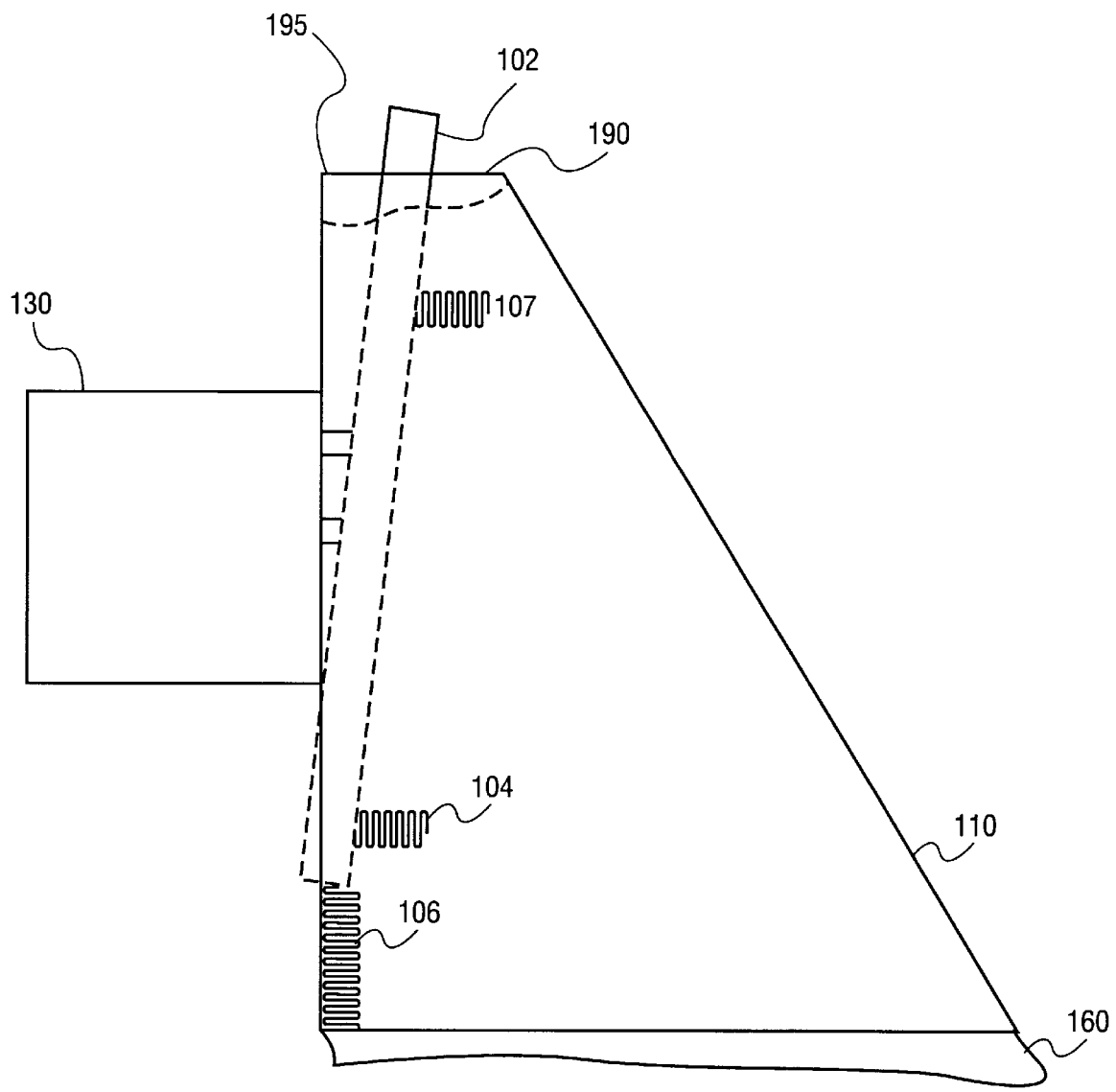
FIG. 3 illustrates a third moveable member in its deactivated state in accordance with one embodiment of the invention.
Figure 4:
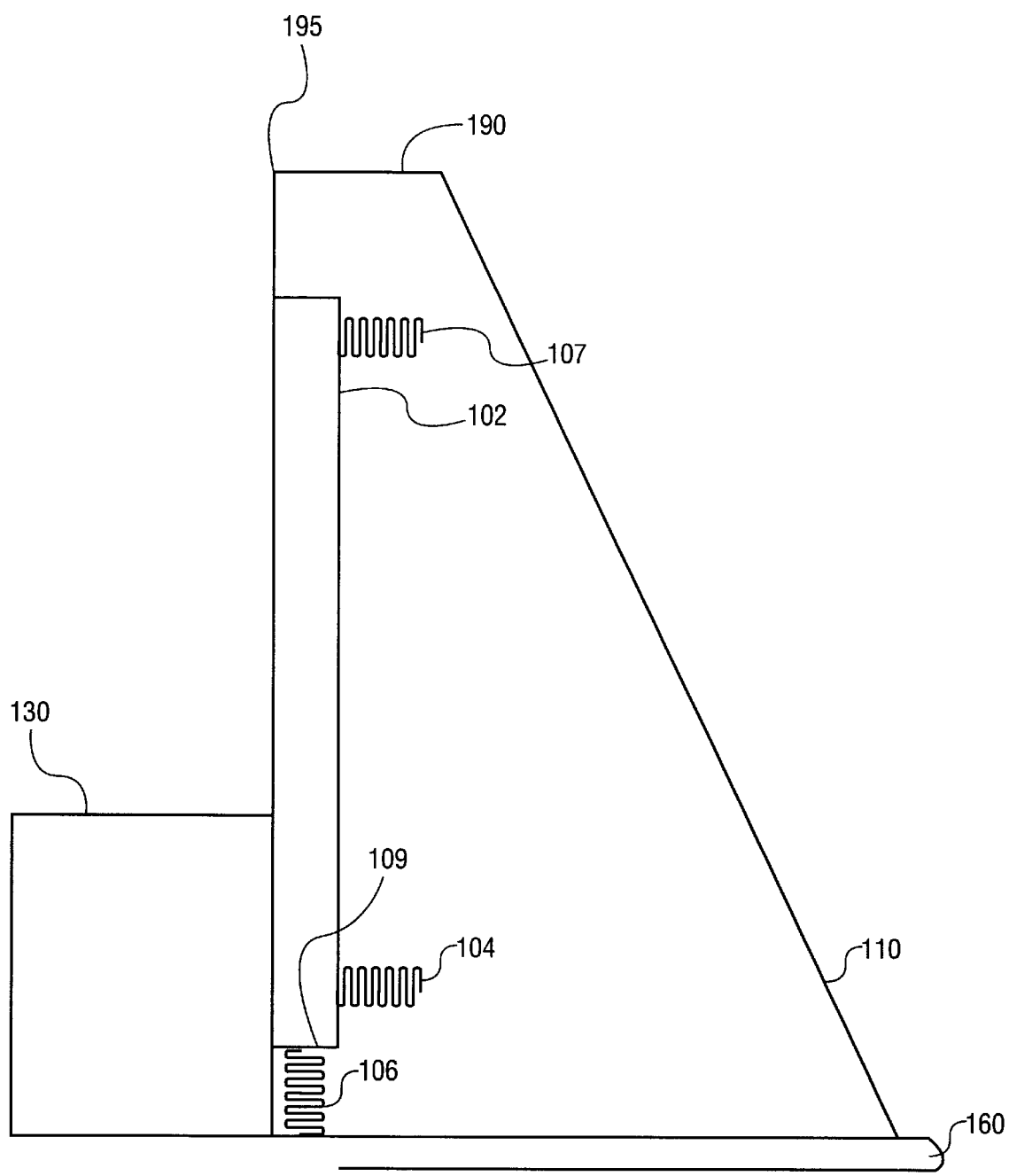
FIG. 4 illustrates a third moveable member in its activated stated in accordance with one embodiment of the invention.

Moveable second member 130 has a top surface that is located at first position $Y_1$. A lever 190, located at the top surface of housing 110, moves, rotates, or pivots about point 195. When lever 190 pivots from the first position $Y_1$ to second position $Y_2$, a trigger mechanism works in connection with spring 140, and moveable second member 130. Spring 140 compresses using conventional techniques allowing the distal tip of first member to pierce the skin of a patient as illustrated in FIG. 2. In another embodiment, the trigger mechanism can include any device capable of causing moveable second member 130 to advance from a first position to a second position.

FIG. 2 illustrates, the port access system 100 after lever 190 has been rotated from a first position $Y_2$, to a second position $Y_{12}$. The top surface of moveable second member 130 has moved from position $Y_1$, to position $Y_2$. The bottom surface of moveable second member 130 contacts or is close to the skin of the patient. Port access system 100 is now ready for infusion of fluids into a patient. Lever 190 is located adjacent to port 120. Port 120 is configured to receive an intravenous line ("IV"). The IV is inserted through aperture 210. It will be appreciated that port 120 can have a variety of shapes in order to receive a variety of various shaped IVs. For example, port 120 may have a shape that is substantially rectangular, circular, a triangle or any other suitable shape.

In one embodiment, the moveable second member 130 may move from its deactivated state to its activated state by using a moveable third member 102. A slot (not shown) exists between moveable third member 102 and moveable second member 130 allowing the coupling member (not shown) between the second and moveable third members (130, 102) to easily move within the slot (not shown). Moveable third member 102, coupled to moveable second member 130, moves from its position shown in FIG. 3 to its position in FIG. 4 using conventional means such as a lever, trigger button, or any other suitable means. A first spring may optionally be used to cause third member 102 to move faster in the horizontal direction. As moveable second and third member (130, 102) moves in a downward direction, second and third springs (104, 106) are energized. Third moveable member 107 snaps into place at locking member 109. Moveable second member 130 advances until the bottom surface of moveable second member 130 contacts or is close to the skin of the patient as shown in FIG. 2.

The needle is activated by pressing down on the moveable second member 130 which then allows infusion of the needle with a channel built into the device that connects to a hub or female leur and infusion may begin. When therapy is completed, the moveable first member is deactivated and returns to its original protective housing. The moveable first member may be deactivated using a variety of methods such as returning lever 190 to its first position $Y_1$, which causes third moveable member 102 to move up by spring 106 returning to a relaxed position. The port access system device is then removed and discarded in accordance with applicable environmental regulations.

In order for moveable second and third member to return to their original position, locking member 109 is released by a trigger button, a latch that is mechanically disengaged, or other suitable means once treatment is completed. Springs (104, 106) relax causing the moveable second and third member (130, 102) to advance vertically back to its original position.

Figure 5:
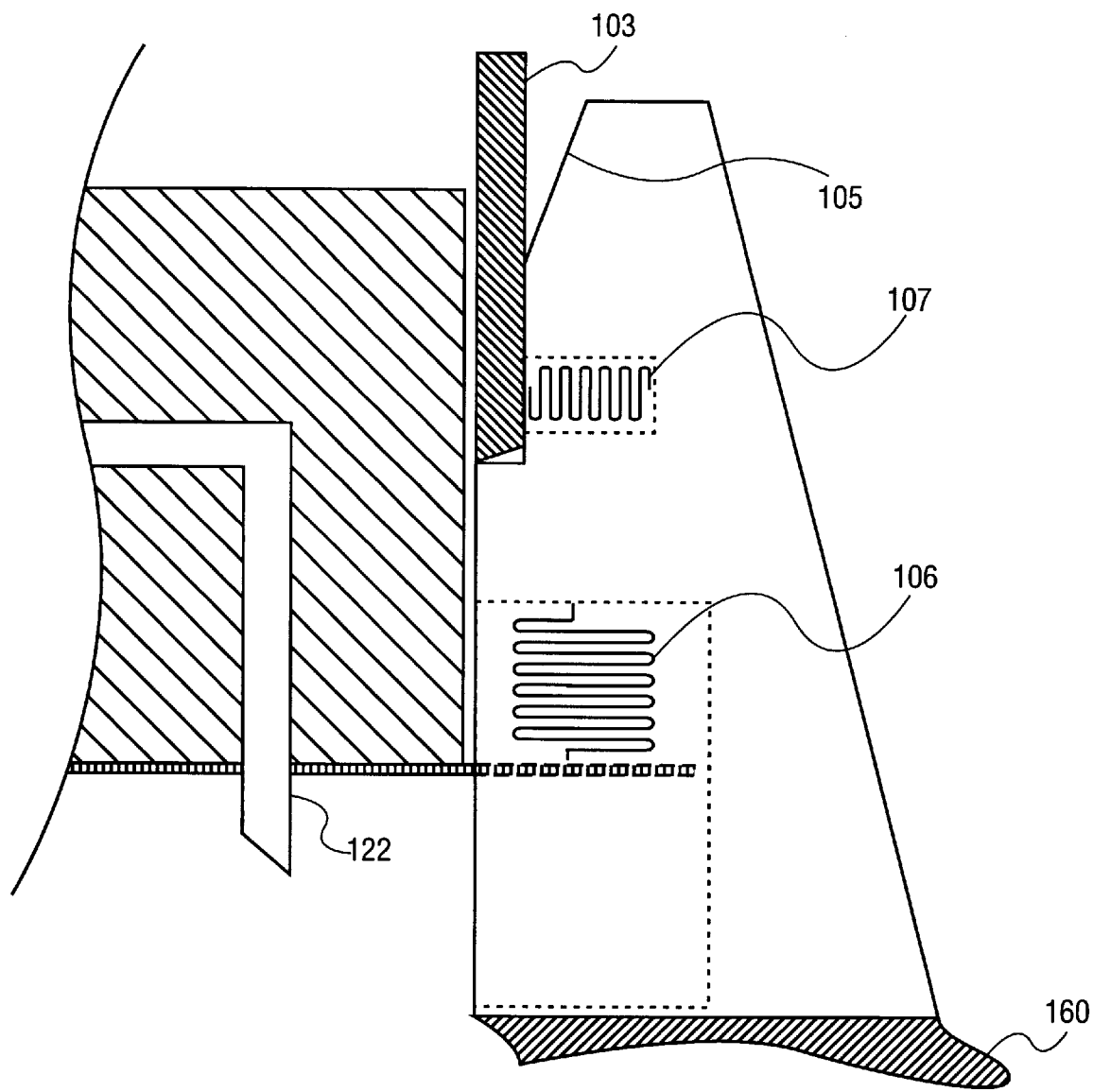
FIG. 5 illustrates a shortened third moveable member in a deactivated state in accordance with one embodiment of the invention.
Figure 6:
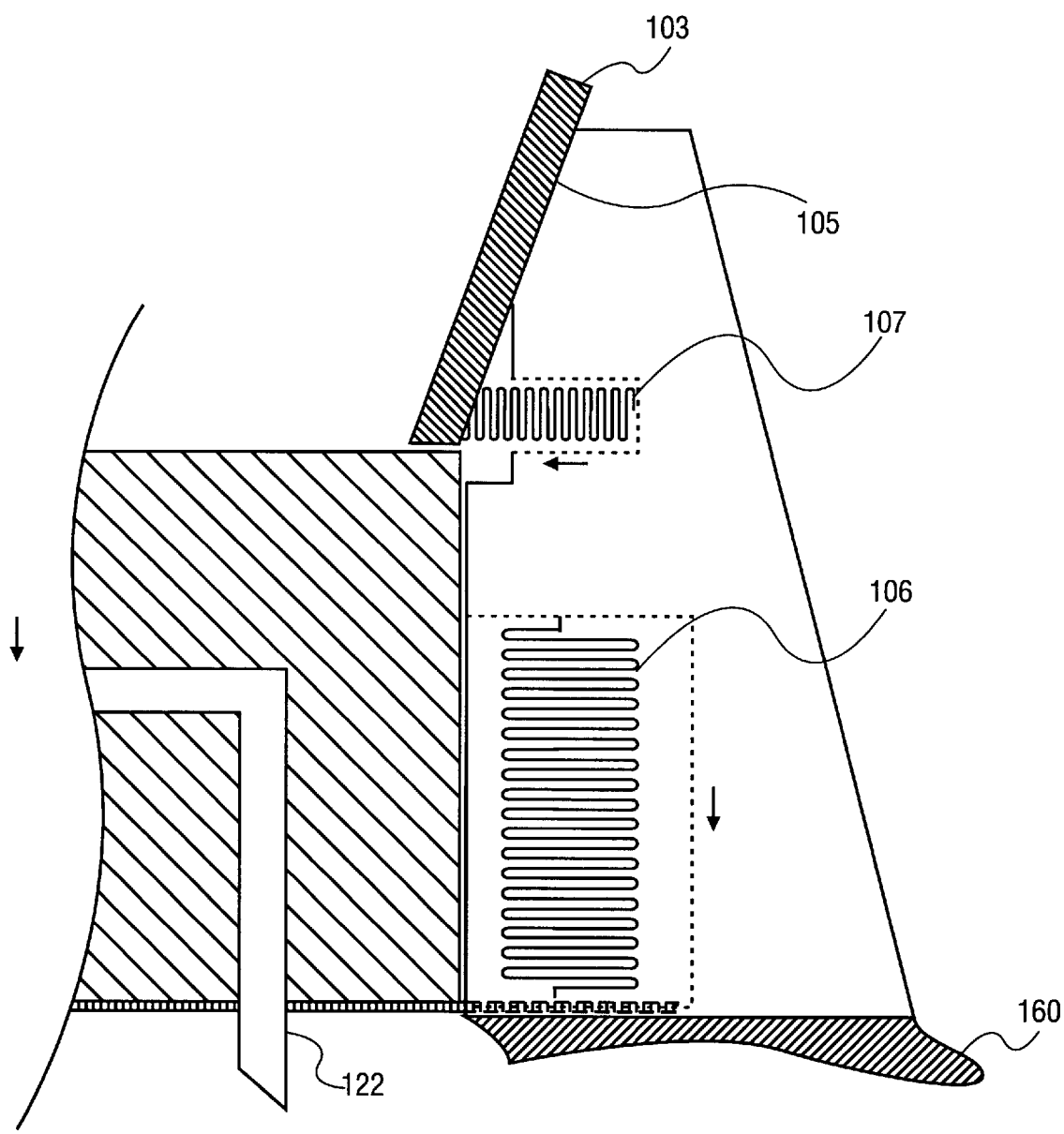
FIG. 6 illustrates a shortened third moveable member in its activated state in accordance with one embodiment of the invention.

FIGS. 5 and 6 illustrate yet another embodiment for moving second and third members (130, 102). FIG. 5 illustrates a shortened third member 103 in a deactivated state. Third member 103 is adjacent to the top inner portion 105 of housing 110. Spring (106) is relaxed. When second moveable member 130 is moved by hand or other suitable means in a downward direction, moveable first member 122 pierces the skin of the patient as illustrated in FIG. 6. FIG. 6 also illustrates the top of third moveable member resting against top inner portion 105 of housing 110. Spring (107) causes the bottom portion of moveable third member 103 to move away from the inner portion of housing 110.

Second moveable member 130 returns to its deactivated position when the top portion of third moveable member 103 is pushed or pulled toward the center of housing 110 causing spring 107 to return to its energized position. Spring 106 returns to its relaxed position and pushes moveable second member 130 back to its deactivated position.

It will be further appreciated that there are numerous ways in which to cause moveable second member 130 to move. For example, moveable second member 130 may be moved from a first position to a second position by a person simply contacting with his or her hand the top surface of moveable member 130. Alternatively, the moveable member 130 may be coupled to a device that allows a person to activate it by contacting an activation button (not shown). The activation button may be a button coupled to a moveable second member 130 that causes the moveable first member 122 to move from its first position in a deactivated state to its second position activated state using conventional means.

Figure 7:
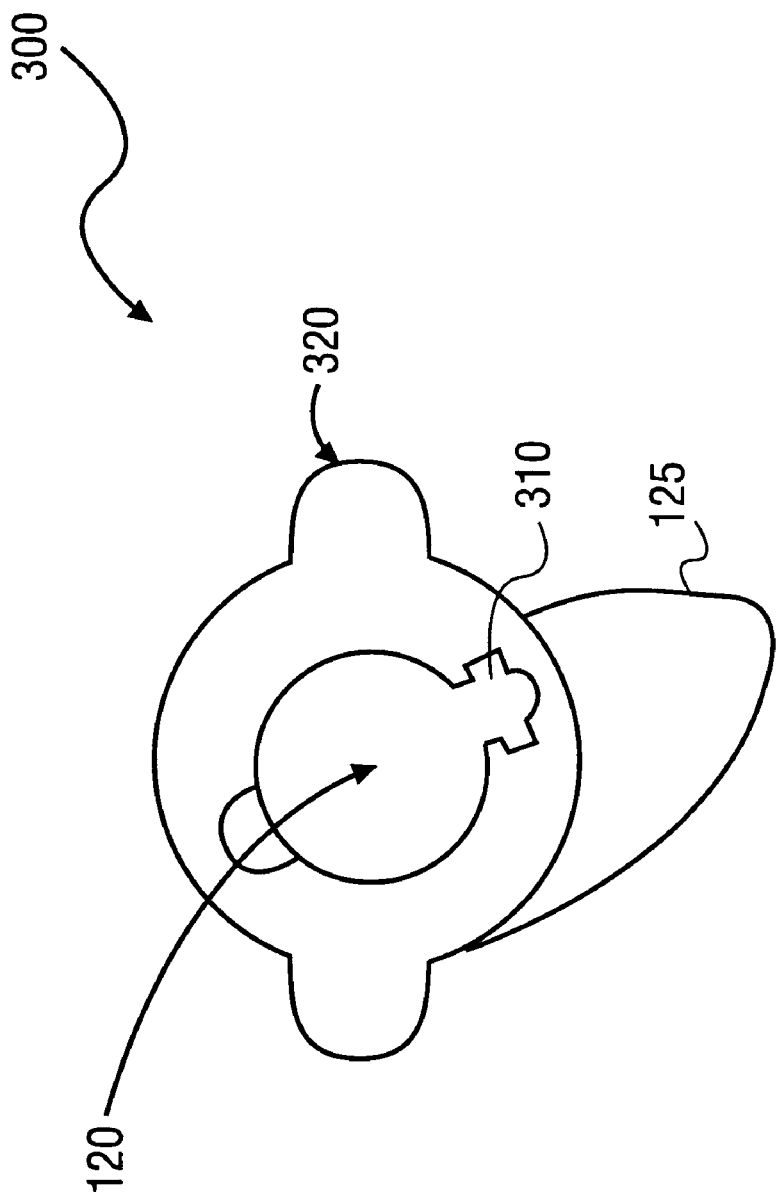
FIG. 7 illustrates a top view of a port in accordance with one embodiment of the invention.

FIG. 7 illustrates a top view 300 of port 120 of funnel-like body 125. Protruding members 320 allow for attachment by a device used to place fluids into a body of a patient. This allows the funnel-like body to be securely in place while an IV is inserted through port 120 and liquids are placed into the IV that is inserted into the patient. Aperture 310 allows IV to lock into place. Upon the IV locking into place, a clicking noise may be heard.

Figure 8:
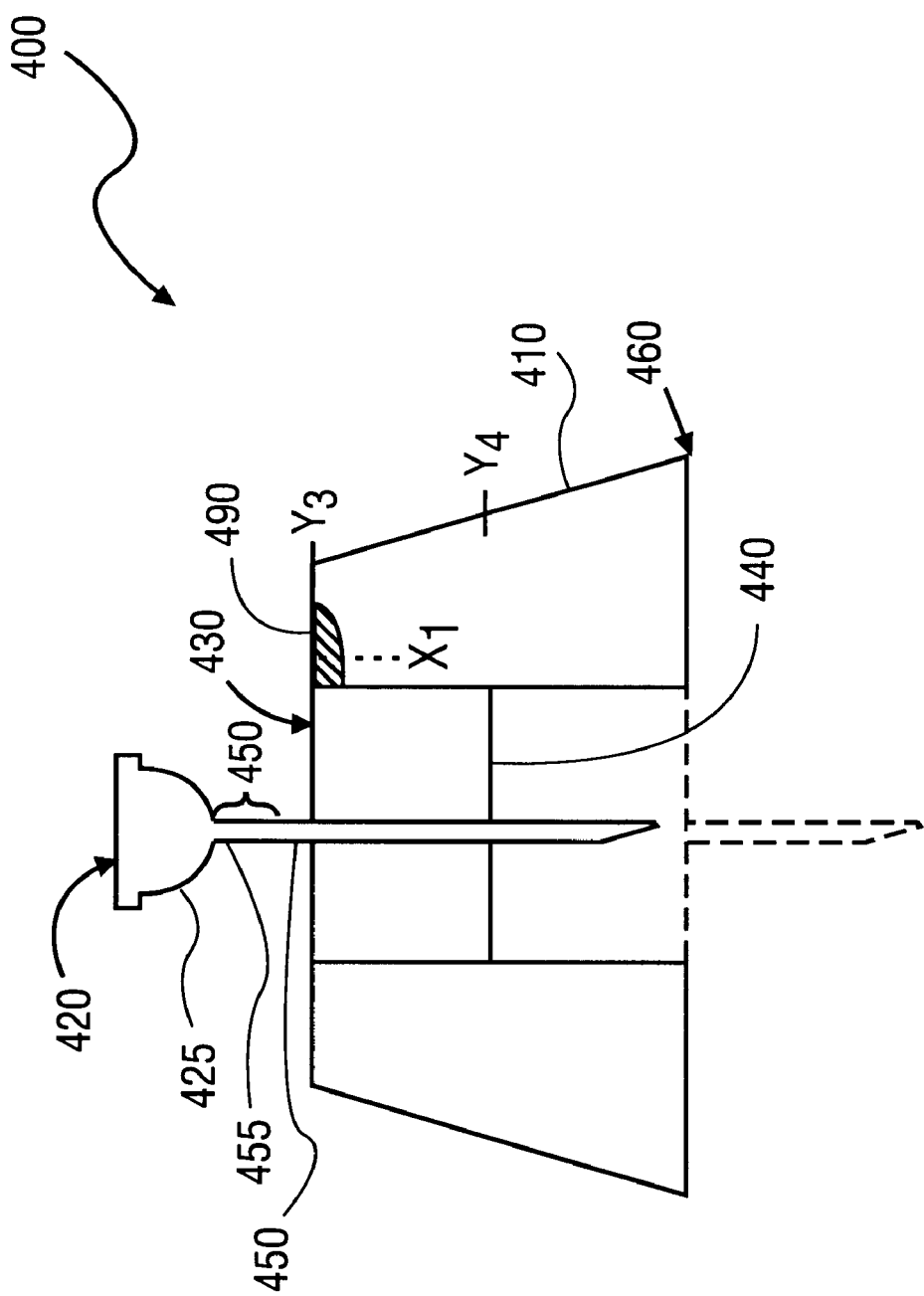
FIG. 8 illustrates a port access system with a moveable member in accordance with one embodiment of the invention.

FIG. 8 illustrates a port access system 400 that includes housing 410 which has a bottom surface that contacts the skin of the patient. Housing 410 has a lever 490 that may be moved from position $Y_3$ to $X_1$ in accordance with one embodiment of the invention. This results in moveable member 430 to drop to position $Y_4$ such that the bottom surface 440 comes close to the skin of the patient. A substantially circular opening 420, which receives fluids, transitions to funnel-like body 425 that receives the fluid(s) that enter port 420. Inlet 455 of funnel-like body 425 allows fluids to flow in through tube portion 450 and then into the shaft of the needle after the needle has been inserted into the patient's body. In this embodiment, tube portion 450 and the shaft of the needle are in a substantially straight alignment in contrast to the angled alignment shown in FIGS. 1–2.

Figure 9:
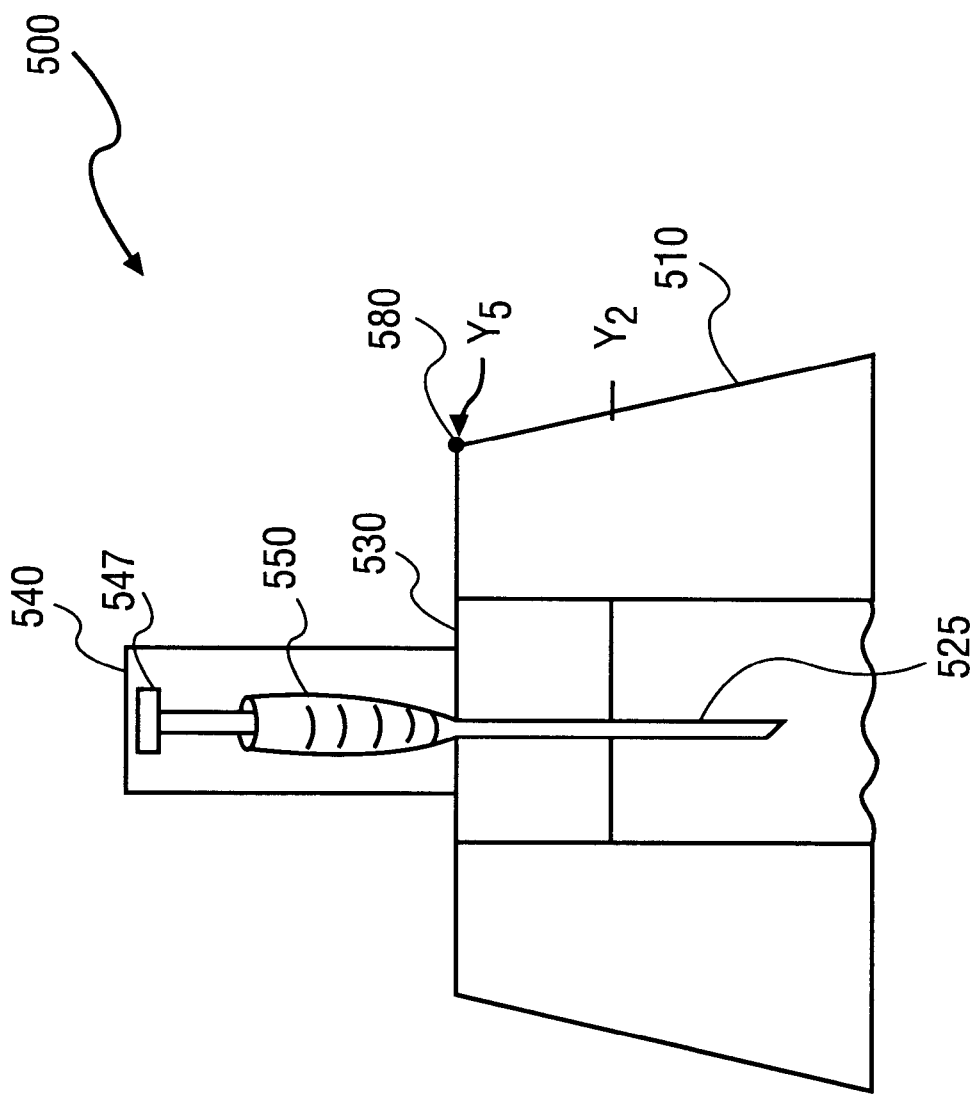
FIG. 9 illustrates a port access system in a first position in accordance with one embodiment of the invention.
Figure 10:
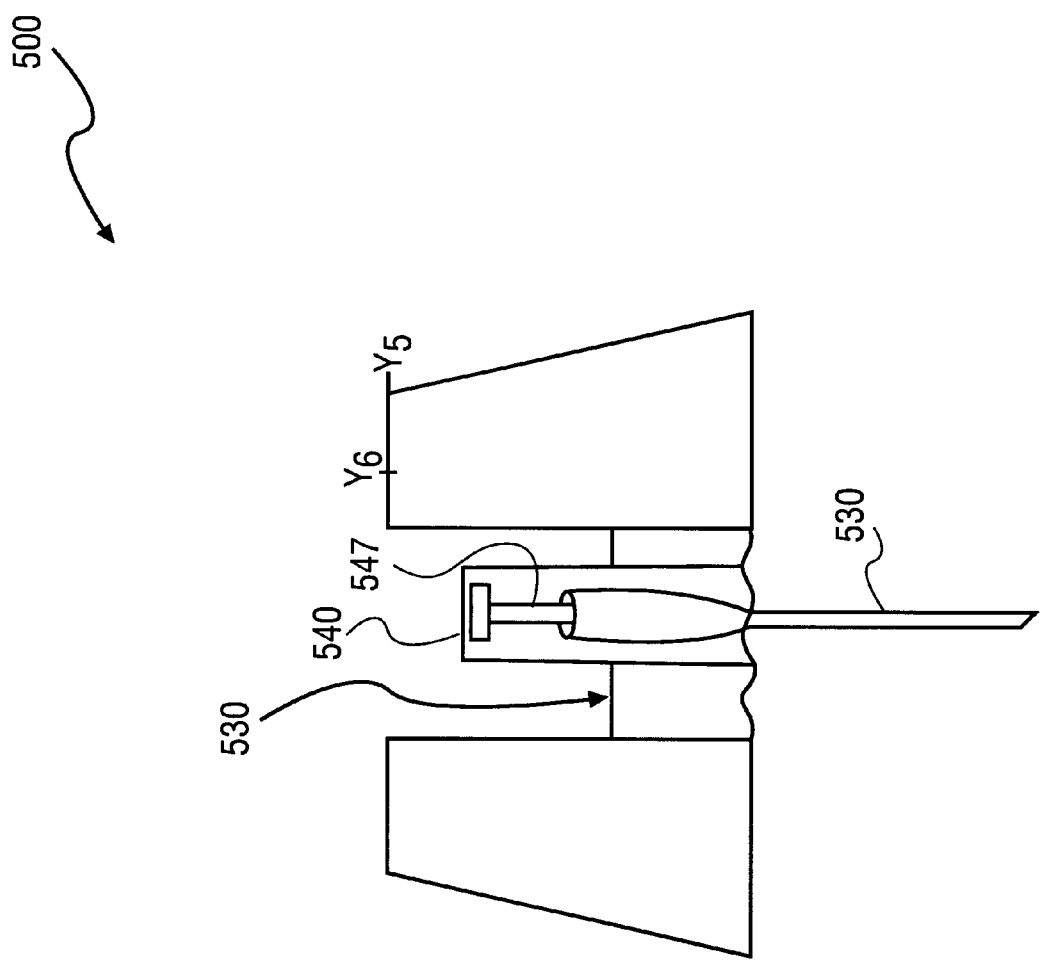
FIG. 10 illustrates the port access system after the moveable member has been activated to advance from one position to another position in accordance with one embodiment of the invention.
Figure 11:
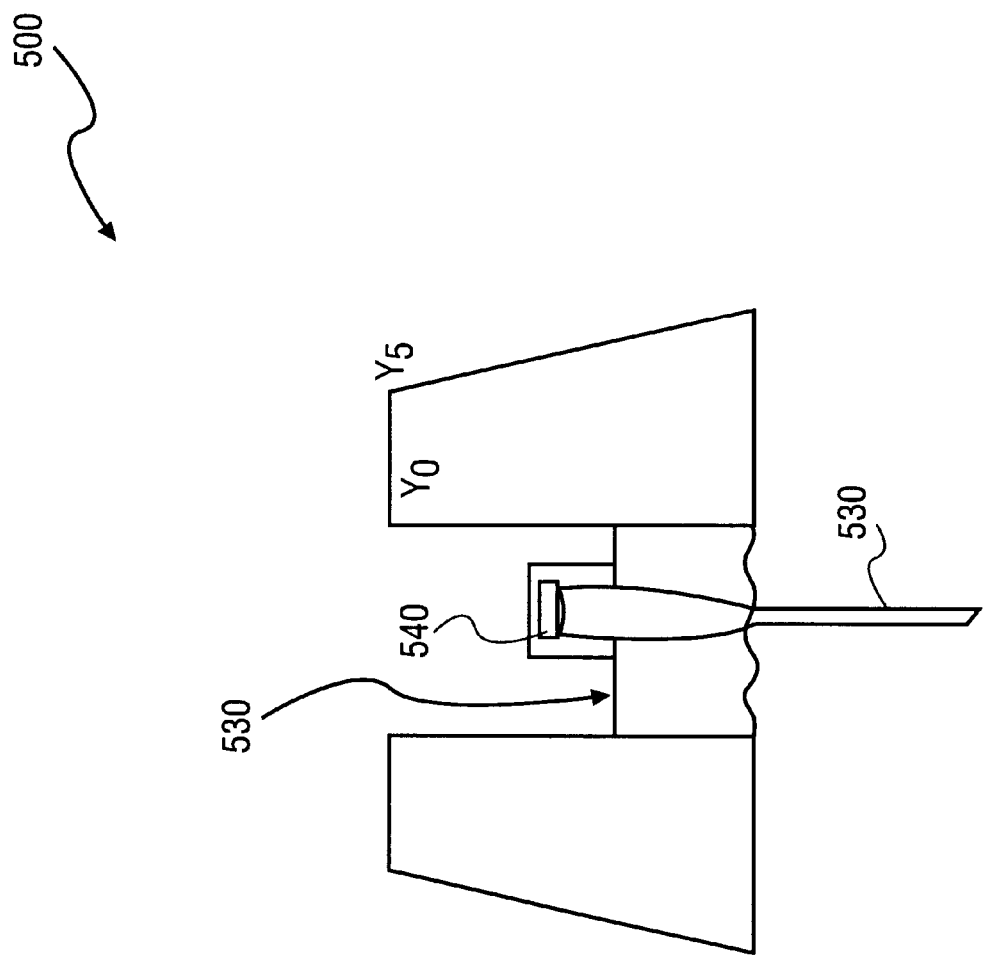
FIG. 11 illustrates a port access system after the syringe has been depressed position in accordance with one embodiment of the invention.

FIGS. 9–11 illustrate another embodiment of port access system 500 that includes housing 510 which provides a secure location for needle 525. In this embodiment, syringe 550 is attached to needle 525. Needle 525 is secured to moveable member 530. Compression member 540 is coupled to plunger 547 of syringe 550. FIG. 9 illustrates moveable member 530 is in a deactivated state in position $Y_5$ in which the top surface of moveable member 530 is located at position $Y_5$.

FIG. 10 illustrates that moveable member 530 has moved from a first position $Y_5$ to position $Y_6$ using conventional means. As a result, needle 525 has punctured the skin and entered a blood vessel or tissue of the patient. FIG. 11 illustrates the same device as in FIG. 10 except the plunger 547 has been depressed using conventional means such as pushing directly on compression member 540 or alternatively, compression member 540 is automatically pushed down once activation button 580 is depressed. Port access system 500 is then removed and disposed of in accordance with environmental regulations.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
    a housing having a port and a tube portion in communication with the port, the tube portion configured to communicate with a moveable first member;
    a moveable second member coupled to the moveable first member, the moveable second member configured to communicate with the tube portion and to move from a retracted position to an extended position;
    a first spring coupled to the housing and the moveable second member to bias the second moveable member to the retracted position;
    a moveable third member coupled to the moveable second member; and
    the moveable third member coupled to at least one second spring.

2. The apparatus of claim 1, wherein the moveable first member is a needle.

3. The apparatus of claim 1, wherein the moveable second member is coupled to the housing and to a trigger member.

4. The apparatus of claim 3, wherein the trigger member is moved from a fast position to a second position causing a noise to be emitted.

5. The apparatus of claim 3, wherein a lever is coupled to the trigger mechanism.

6. The apparatus of claim 5, wherein the lever is moved and causes the trigger mechanism to automatically move.

7. The apparatus of claim 5, wherein the needle is one of an angled needle and a straight needle.

8. The apparatus of claim 1, further comprising at least one wing located at an inlet of the port.

9. The apparatus of claim 8, further comprising one of an adhesive material or a foam pad, and a foam pad with adhesive located at a bottom surface of the wing.

* * * * *